United States Patent [19]

Marchase et al.

[11] Patent Number: 5,643,883
[45] Date of Patent: Jul. 1, 1997

[54] GLUCOSE-6-PHOSPHATE UPTAKE INHIBITORS AND NOVEL USES THEREOF

[75] Inventors: Richard B. Marchase; Sudha Darbha, both of Birmingham, Ala.

[73] Assignee: UAB Research Foundation, Birmingham, Ala.

[21] Appl. No.: 376,048

[22] Filed: Jan. 19, 1995

[51] Int. Cl.⁶ .......................... A01N 43/04; A61K 31/70
[52] U.S. Cl. .................. 514/23; 514/62; 514/724; 514/727; 514/729; 514/738; 514/740
[58] Field of Search ............................. 514/729, 724, 514/727, 738, 740, 23, 62

[56] References Cited

PUBLICATIONS

CA 120:131,345 (1994).

*Primary Examiner*—James J. Seidleck
*Assistant Examiner*—John M. Cooney, Jr.
*Attorney, Agent, or Firm*—Benjamin Aaron Adler

[57] ABSTRACT

The present invention provides a composition of matter comprising an inhibitor of glucose-6-phosphate uptake. Also provided is a method of inhibiting the import of glucose-6-phosphate into the endoplasmic reticulum of a cell, comprising the step of adminstering a pharmacologically effective dose of a glucose analogue to said cell. Further provided is a method of inhibiting intracellular endoplasmic reticular concentrations of calcium, comprising the step of administering to a cell a pharmacologically effective dose of a glucose-6-phosphate uptake inhibitor.

7 Claims, 13 Drawing Sheets

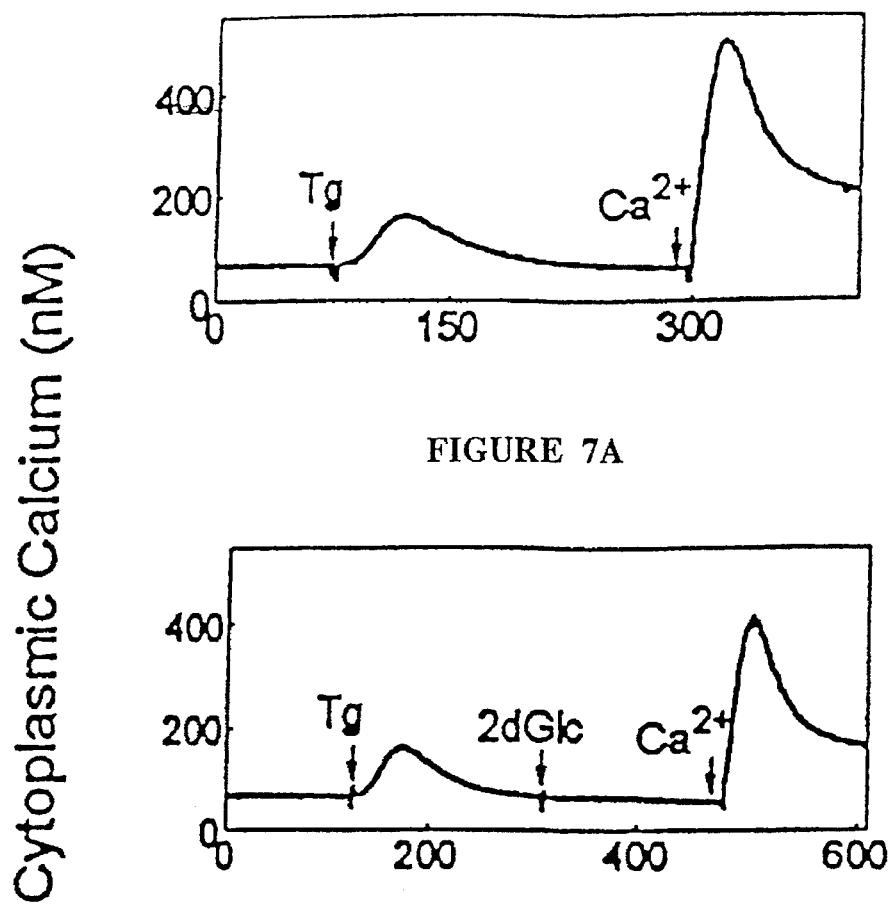
FIGURE 7A
FIGURE 7B
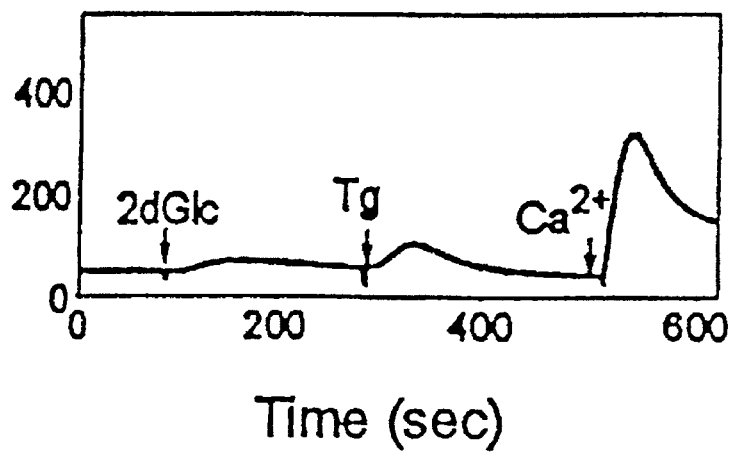
Time (sec)
FIGURE 7C

5,643,883

GLUCOSE-6-PHOSPHATE UPTAKE INHIBITORS AND NOVEL USES THEREOF

BACKGROUND OF THE INVENTION

1. Field of the Invention

The present invention relates generally to the fields of allergy, immunology and cell biology. More specifically, the present invention relates to novel inhibitors of glucose-6-phosphate uptake and methods of using such glucose-6-phosphate uptake inhibitors to treat specific diseases.

2. Description of the Related Art

The inositol (1,4,5)tris-phosphate (IP$_3$)-mediated release of calcium sequestered within the endoplasmic reticulum into the cytoplasm is an early step in a host of signal transduction cascades, including those initiated by ligation of antigen receptors in cells of the immune system. In unstimulated cells, calcium is sequestered within the endoplasmic reticulum to concentrations on the order of 10 mM through the action of calcium ATPases found in the membranes of the endoplasmic reticulum or its analogue in muscle, the sarcoplasmic reticulum. In addition to this pump, a mechanism for "buffering" intra-organellar calcium is also essential, since a free intra-organellar calcium concentration of 1 mM inhibits further sequestration. High-capacity, low-affinity calcium-binding proteins like calsequestrin or calreticulin within the endoplasmic reticulum have been proposed to be necessary to decrease the concentration of intra-organellar free calcium and allow the ATPase to continue to function. However, Volpe et al. determined that 3.6 mM calcium within the sarcoplasmic reticulum of frog muscle is not associated with calsequestrin and about 75% of the calcium released in response to excitation is not from a calsequestrin-associated pool.

In addition, isolated vesicles derived from the sarcoplasmic reticulum of muscle or the endoplasmic reticulum of other cells exhibit a relatively low calcium accumulating capacity. This capacity can be enhanced to physiological levels through the use of selected anions. In early experiments, high concentrations of Pi or oxalate were used to precipitate calcium and thus allow continued activity of the calcium ATPase. The possibility that anions might be physiologically relevant was first suggested by Chu et al. They found, using high concentrations of succinate, a significantly increased uptake of calcium by sarcoplasmic reticulum vesicles that was matched by the equimolar uptake of the negatively charged succinate, without precipitation. A stoichiometric efflux of the counter-ion was induced when calcium was released with an ionophore. Fulceri and co-workers found in microsomes from both liver and other tissues that physiological levels of P$_i$ also support an enhancement of calcium sequestration. Again, the calcium and the P$_i$ remained soluble, were imported in an equimolar ratio, and were rapidly released stoichiometrically upon treatment with calcium ionophore, IP$_3$, or dilution of either extramicrosomal calcium or P$_i$.

These data provide support for the idea that anions, by forming a soluble complex with calcium, are able to restore the calcium-sequestering capacity of the endoplasmic reticulum to physiological levels and in so doing provide an enlarged pool of calcium for release in response to stimuli. If an anion that is used as a "buffer" for intraorganellar calcium is also imported and exported along with calcium, the need for a compensating current to balance the movement of calcium's charge during both the transport and release processes is also met. However, the relevance of these observations to the physiology of intact cells and the identity of the anion imported into the endoplasmic reticulum, if any, remains undetermined.

An additional anion has been implicated in the enhancement of endoplasmic reticulum calcium stores. Glucose-6-phosphate (G-6-P) is efficiently imported into the endoplasmic reticulum of liver as a step in glycogenolysis. It is cleaved to glucose and P$_i$ by an intra-organellar glucose-6-phosphatase, and the products are then re-exported to the cytoplasm. Benedetti et al. showed that in liver microsomes less than 1 mM glucose-6-phosphate resulted in a 10-fold increase in sequered calcium, while P$_i$ as a counter-ion was much less effective. Similar results were found with microsomes from kidney and pancreatic cells, both of which are characterized by high levels of glucose-6-phosphatase.

Although immune cells have not been reported to possess high levels of glucose-6-phosphatase, glucose analogues have been shown to effect calcium-mediated immune responses; T cell-mediated cytolysis, IgG-mediated phagocytosis by macrophages and neutrophils, and antibody-dependent eosinophil-mediated lysis of schistosomula have been known for many years to be inhibited by the glucose analogue 2-deoxyglucose. Since 2-deoxyglucose leads to a decrease in cellular ATP, its inhibitory effects were not unexpected. However, closer examinations demonstrated that the inhibitory effect was not due to ATP depletion nor to 2-deoxyglucose's inhibitory effect on glycoprotein synthesis. In addition, another 2-carbon derivative of glucose, glucosamine has been shown to act as an anti-reactive and anti-inflammatory and has been used to treat osteoarthritis although the mechanism underlying its efficacy is undetermined.

Other calcium related phenomena as diverse as smooth muscle contractility in response to norepinephrine or pressor hormones, sperm capacitation, and neural transmission both in vivo and in vitro have also been reported to have requirements for glucose independent of total ATP levels. In the case of smooth muscle Zhang and Paul reported that the absence of glucose led to higher than normal cytoplasmic calcium due to ineffective calcium sequestration by the endoplasmic reticulum/sarcoplasmic reticulum. The dependency on glucose was suggested to be due to the presence of an ATP pool generated by glycolysis that is independent of total cellular ATP and necessary to achieve proper calcium sequestration within the endoplasmic reticulum/sarcoplasmic reticulum.

The prior art continues to lack of additional effective means of treating various auto-immune diseases. The present invention fulfills this longstanding need and desire in the art.

SUMMARY OF THE INVENTION

In one embodiment of the present invention, there is provided a composition of matter comprising an inhibitor of glucose-6-phosphate uptake, said inhibitor decreasing the uptake of glucose-6-phosphate by a calcium-sequestering organelle.

In another embodiment of the present invention, there is provided a pharmaceutical composition, comprising an inhibitor of glucose-6-phosphate uptake and a pharmaceutically acceptable carrier.

In yet another embodiment of the present invention, there is provided a method of inhibiting the import of glucose-6-phosphate into the endoplasmic reticulum of a cell, comprising the step of adminstering a pharmacologically effective dose of a glucose analogue to said cell, said analogue being phosphorylated at its 6-carbon after uptake by said cell.

In still yet another embodiment of the present invention, there is provided a method of inhibiting intracellular endoplasmic reticular concentrations of calcium, comprising the step of administering to a cell a pharmacologically effective dose of a glucose-6-phosphate uptake inhibitor.

Other and further aspects, features, and advantages of the present invention will be apparent from the following description of the presently preferred embodiments of the invention given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

FIG. 3 shows the effect of Glc on the thapsigargin-sensitive calcium pool. Fura-2AM loaded J774 cells were suspended in HBS-EGTA containing 5 mM Glc and 5 mM pyruvate.

FIG. 7 shows the capacitative entry of calcium is inhibited by the presence of 2dGlc. J774 cells were loaded with Fura-2AM and resuspended in HBS-EGTA with 5 mM Glc and 5 mM pyruvate. FIG. 7A shows the result when thapsigargin (Tg; 200 nM) was added to deplete the endoplasmic reticulum calcium pool, and the capacitative entry of calcium was then initiated by adding calcium (to a final concentration of 2.5 mM); FIG. 7B shows the result when 2dGlc (25 mM) was added after thapsigargin but prior to the addition of calcium; FIG. 7C shows the result when 2dGlc was added first, followed by the additions of thapsigargin and calcium. Addition of 2dGlc after thapsigargin but for longer time periods prior to the addition of calcium also resulted in a more pronounced inhibition of the calcium influx.

FIG. 8 shows the effects of 2dGlc and Glc on the steady state capacitative entry of calcium.

DETAILED DESCRIPTION OF THE INVENTION

Figure 1A:
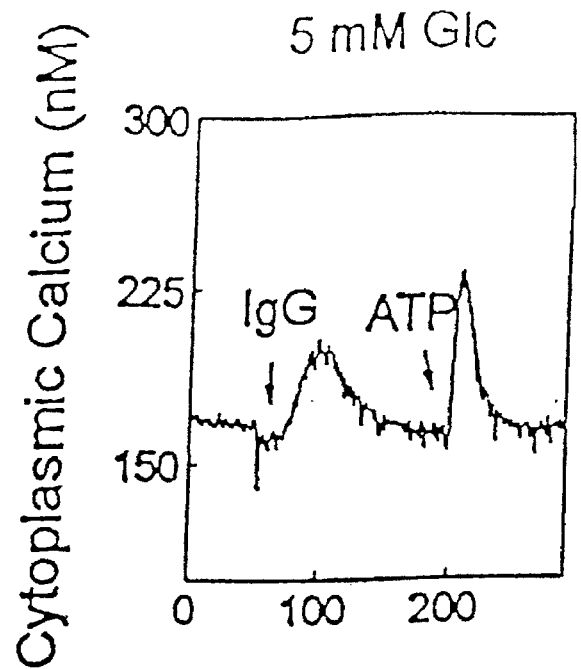
FIG. 1 shows the responses in cytoplasmic calcium to aggregated IgG and ATP in control, 2-deoxyglucose-treated, or glucose-deprived cells. J774 cells were stimulated with aggregated IgG (Agg IgG) and ATP after a 2 minute incubation in the presence of (A) 5 mM glucose, (B) 5 mM glucose, 5 mM pyruvate and 25 mM 2-deoxyglucose and (C) 5 mM pyruvate. J774 cells were grown in DMEM with 10% heat-inactivated fetal bovine serum (GIBCO) and 1% penicillin/streptomycin. The cells were washed in serum-free DMEM and resuspended in DMEM containing 1 mg/ml BSA. The cells were then loaded with 2 mM Fura-2AM (Molecular Probes) at 37° C. in the presence of 2.5 mM probenecid, added to decrease leakage of Fura-2. Parallel experiments were performed in the absence of probenicid with comparable results. After 30 minutes, the cells were centrifuged and resuspended in Hepes-buffered saline (HBS) containing 125 mM NaCl, 5 mM KCl, 5 mM $MgSO_4$, 1 mM $KH_2PO_4$, 1 mM $CaCl_2$, 10 mM $NaHCO_3$, 20 mM HEPES, pH 7.4. Glucose, pyruvate and 2-deoxyglucose were added as indicated. Aggregated IgG was prepared by incubating human IgG at 63° C. for 30 minutes. The pellet obtained after ultracentrifugation at 145,000× g for 1 hour was collected and homogenized in phosphate buffered saline, pH 8.0, at 5 mg/ml. 100 ml were added to stimulate the cells. Mg-ATP was added at a final concentration of 10 mM. Fluorescence measurements were performed using a fluorescence spectrophotometer (SPEX Industries Inc.) with the cells suspended in a cuvette in a temperature-controlled chamber (37° C.) equipped with a magnetic stirrer. Fluorescence intensity was measured at an emission wavelength of 500 nm with excitation wavelengths of 340 nm and 380 nm. [Calcium]$_i$ was calculated as previously described. Comparable results were seen when the concentrations of glucose and 2-deoxyglucose were 1 and 5 mM, respectively.

In the present invention, it is shown that glucose and, in particular, its metabolite glucose-6-phosphate are important to calcium-regulated processes not solely for the generation of ATP but rather because they provide the anion necessary for efficient calcium regulation by the sequestering organelle. This appears to include both the sequestration of calcium as well as the secondary entry of calcium across the plasma membrane referred to as capacitative calcium influx. The relevance of this need for glucose-6-phosphate import to calcium-mediated processes underlying a host of signal transduction pathways including but not limited to immune responses comprises the present invention.

The present invention is directed to a composition of matter comprising an inhibitor of glucose-6-phosphate uptake. The inhibition of glucose-6-phosphate uptake is from the endoplasmic reticulum and other calcium sequestering organelles. It is specifically contemplated that pharmaceutical compositions may be prepared using novel inhibitors of glucose-6-phosphate uptake in the novel methods of the present invention. In such a case, the pharmaceutical composition comprises the inhibitor of glucose-6-phosphate uptake of the present invention and a pharmaceutically acceptable carrier. A person having ordinary skill in this art would readily be able to determine, without undue experimentation, the appropriate dosages and routes of administration of the inhibitor of glucose-6-phosphate uptake of the present invention.

The present invention also provides a method of inhibiting the import of glucose-6-phosphate into the endoplasmic reticulum of a cell, comprising the step of adminstering a pharmacologically effective dose of a glucose analogue to said cell, said analogue being phosphorylated at its 6-carbon after uptake by said cell. Generally, any glucose analogue which is phosphorylated at its 6-carbon by hexokinase and then competes with glucose-6-phosphate for uptake by an intracellular organelle is useful in the methods of the present invention. In one embodiment, the analogue is modified at the number 2 carbon.

Generally, the inhibitors of glucose-6-phosphate uptake by intracellular organelles useful in the novel methods of the present invention are competitive inhibitors of glucose-6-phosphate uptake. Representative examples of such competitive inhibitors of glucose-6-phosphate uptake include 2-deoxyglucose-6-phosphate, glucosamine-6-phosphate and N-acetylglucosamine-6-phosphate. This inhibition is achieved, as noted above, by exposing the intact cells to the corresponding sugars (e.g., 2-deoxyglucose, glucosamine and N-acetylglucosamine) which are imported into the cell and phosphorylated at the 6-carbon to produce the actual inhibitory substances.

Generally, the inhibitors of glucose-6-phosphate uptake useful in the novel methods of the present invention are administered to the cell in a concentration sufficient to significantly decrease glucose-6-phosphate uptake. Thus, such inhibitors are generally administered to said cell at a concentration of from about 0.1 mM to about 20 mM. Generally, the inhibitor is given by a route of administration selected from the group consisting of oral administration, intranasal administration and inhalation administration, although other routes of administration are recognizable to one having ordinary skill in this art.

The present invention also provides a method of inhibiting intracellular endoplasmic reticular concentrations of calcium, comprising the step of administering to a cell a pharmacologically effective dose of a glucose-6-phosphate uptake inhibitor. For any of the methods of the present invention, the glucose-6-phosphate uptake inhibitors may be either competitive or non-competitive inhibitors.

The following examples are given for the purpose of illustrating various embodiments of the invention and are not meant to limit the present invention in any fashion.

EXAMPLE 1

Cell Culture

J774 cells (American Type Culture Collection) were cultured at 37° C. in Dulbecco's modified Eagle's medium (DMEM) supplemented with 10% fetal calf serum (GIBCO-BRL) and 1% penicillin/streptomycin in a humidified environment of 90% air and 10% $CO_2$.

EXAMPLE 2

Buffers and Stimulants

HEPES-based saline solution (HBS): 125 mM NaCl, 5 mM KCl, 5 mM $MgSO_4$, 1 mM $KH_2PO_4$, 10 mM $NaHCO_3$, 5 mM pyruvate, 20 mM HEPES, pH 7.3. HBS-Ca: HBS containing 1 mM $CaCl_2$. HBS-EGTA: HBS with 1 mM EGTA. IB: Intracellular-like buffer with 110 mM KCl, 10 mM NaCl, 2 mM $MgCl_2$, 5 mM $KH_2PO_4$, 20 mM HEPES, pH 7.2. Aggregated IgG was prepared by incubating human IgG (Sigma Chemical Co.) at 63° C. for 30 minutes. Ultra-centrifugation was performed at 145,000× g for 1 hour at 4° C., and the resulting pellet was homogenized and resuspended in phosphate-buffered saline (PBS), pH 8.0. IgG (250 g/ml) was were used to stimulate the J774 cells. Mg-ATP (Sigma) was used at a final concentration of 10 mM.

EXAMPLE 3

Measurement of cytoplasmic calcium with Fura-2AM

J774 cells were washed in serum-free DMEM and resuspended in DMEM containing 1 mg/ml BSA and 2.5 mM probenecid. Probenecid was added to decrease the leakage of Fura-2. In nearly all cases, parallel studies were done in the absence of probenecid and comparable results were obtained. Fura-2AM (Molecular Probes) was added to a final concentration of 2 mM. After a 30 minute incubation at 37° C. the cells were centrifuged, washed and resuspended in HBS. Fluorescence measurements were performed in a fluorescence spectrophotometer (Spex Industries Inc.) with the cells suspended in a cuvette in a temperature-controlled chamber (37° C.) equipped with a magnetic stirrer. The fluorescence intensity was measured at 500 nm with excitation wavelengths of 340 and 380 nm. $[Ca^{2+}]_i$ was calculated as described by Grynkiewicz et al (1985). That is, $[Ca^{2+}]_i = K_d \times (R-R_{min})/(R_{max}-R) \times S_{f2}/S_{b2}$, where $K_d$ is the Fura-2 dissociation constant for $Ca^{2+}$ (224 nM), R is the ratio of the intensities at 340 nm and 380 nm, and $R_{min}$ and $R_{max}$ are the R values at 0 and saturating levels of $Ca^{2+}$ respectively. $S_{f2}/S_{b2}$ is the ratio of the intensities at 380 nm excitation under $R_{min}$ and $R_{max}$ conditions. $Ca^{2+}$ concentrations in permeabilized cells using the Fura-2 pentapotassium salt at 2 mM were calculated in an identical manner.

EXAMPLE 4

Assays for intracellular ATP levels

Cellular ATP levels were determined using an ATP assay kit (Calbiochem) based on firefly luciferase-catalyzed oxidation of d-luciferin. The emitted light was quantitated by luminometry (Analytical Luminescence Laboratory). Cells ($10^5$/ml) were incubated in HBS-Ca containing the indicated nutrients or inhibitors for 4 minutes. A 10 ml aliquot was then added to the kit's releasing agent and the reaction was initiated by addition of the enzyme. ATP calibrations containing the sugars and inhibitors were assessed and none interfered with the assay.

EXAMPLE 5

Preparation of rat liver microsomes and $^{45}Ca$ Uptake assays

Liver microsomes were isolated as previously described (Benedetti et al., 1985). Briefly, a liver homogenate in 0.154M KCl and 3 mM EDTA at pH 7.4 was centrifuged at 2700× g for 10 minutes. The resulting supernatant was centrifuged at 80,000× g for 30 minutes. This pellet was resuspended at 5 mg/ml in 100 mM KCl, 30 mM imidazole-histidine buffer, pH 7.2. $^{45}Ca^{2+}$ uptake assays were performed as reported (Benedetti et al., 1985). The assay buffer was: 100 mM KCl, 30 mM imidazole-histidine (pH 7.2) 5 mM sodium azide, 5 mM $MgCl_2$, 5 mM ATP, 20 mM $CaCl_2$, and 0.1 mCi/ml $^{45}CACl_2$ (NEN-Dupont). Glc-6-P and 2dGlc-6-P were added as noted. A 0.1 ml aliquot of the microsomal suspension was added to 5 ml assay buffer. Sample aliquots of 500 µl were withdrawn at the indicated times and filtered through prewet cellulose nitrate filters (pore size 0.2 mm). The filters were washed with 100 mM KCl, 30 mM imidazole-histidine buffer (pH 7.2) and placed in 5 ml of scintillation fluid. Radioactivity was monitored using a Packard Tri-Carb 4000 scintillation counter.

EXAMPLE 6

Regulation of intracellular calcium by glucose metabolites 2-deoxyglucose, independent of its effects on ATP levels and glycoprotein synthesis, has been shown to inhibit several immune reactions initiated by ligation of antibody receptors and leading to inositol (1,4,5) tris-phosphate-mediated calcium release. In the J774 murine macrophage-like cell line, 2-deoxyglucose caused an inhibition of calcium transients in response to aggregated IgG and ATP by depleting calcium from thapsigargin-sensitive intracellular pools. In parallel studies with permeabilized cells, glucose-6-phosphate, but not 2-deoxyglucose-6-phosphate, increased the amount of ATP-dependent sequestered calcium. Thus, there is a physiological role for glucose metabolism in which glucose-6-phosphate is necessary for calcium sequestration within the endoplasmic reticulum. In addition, the capacitative influx of extracellular calcium following depletion of intracellular stores was inhibited by 2-deoxyglucose or glucose deprivation.

In macrophages, the phagocytosis of IgG-coated particles is initiated by a transient increase in cytoplasmic calcium following activation of cell-surface $F_c$ receptors. When intracellular stores are depleted and not allowed to refill, subsequent phagocytic events can no longer be initiated. The ability of both macrophages and neutrophils to engulf IgG-coated particles was also compromised by the presence of the glucose analogue 2-deoxyglucose, which was efficiently internalized and converted to 2-deoxyglucose-6-phosphate (but not metabolized to ATP). Studies with alternate substrates and other inhibitors showed that this inhibition was not due to limitations in ATP nor to inhibitory effects on protein or glycoprotein synthesis. The present invention shows that 2-deoxyglucose was interfering with calcium signaling during this process and investigated this possibility using J774 cells, a murine macrophage-like cell line that has a well-characterized $F_c$ receptor and exhibits predominantly antibody-dependent phagocytosis.

Figure 1B:
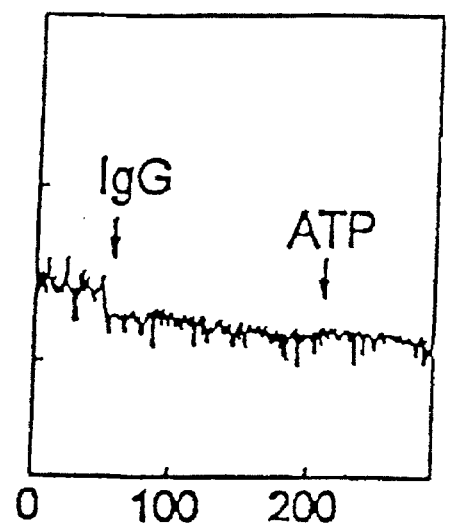
Figure 1C:
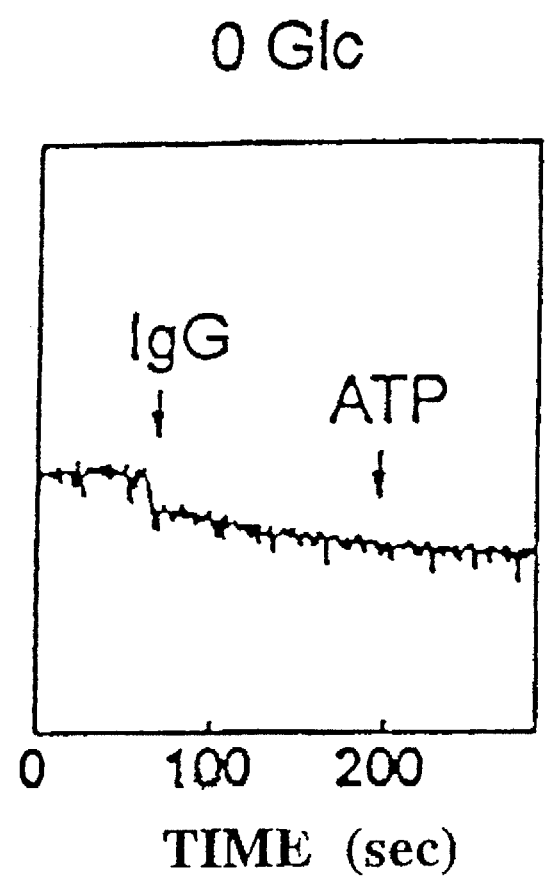

Free cytoplasmic calcium levels ([calcium]$_i$) were monitored using the ratiometric calcium indicator Fura-2. As shown in FIG. 1A, stimulating the $F_c$ receptor with aggregated IgG resulted in a transient increase in cytoplasmic calcium and subsequent stimulation of a purinergic receptor with 10M ATP elicited an additional calcium response. However, a 2 minute preincubation in pyruvate and a 5-fold excess of 2-deoxyglucose relative to glucose abolished both of these responses (FIG. 1B). Depriving the cells of glucose but providing pyruvate had an equally profound effect (FIG. 1C.).

Figure 2A:
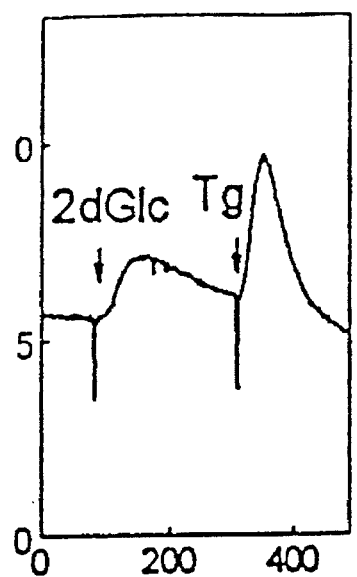
FIG. 2 shows the effect of 2-deoxyglucose or NaF on the thapsigargin-sensitive calcium pool. Fura-2AM loaded J774 cells were resuspended in calcium-free HBS containing 5 mM glucose, 5 mM pyruvate and 1 mM EGTA. 2-deoxyglucose (25 mM) was added either (FIG. 2A) prior to the addition of 200 nM thapsigargin (Tg) or (FIG. 2B) after the depletion of calcium pools by thapsigargin.
In FIG. 2C, the effects of 1 mM NaF, added prior to the addition of thapsigargin, is shown. Results comparable to those with NaF were seen following addition of the non-metabolizable glucose analogue 5-thioglucose (data not shown).
Figure 2B:
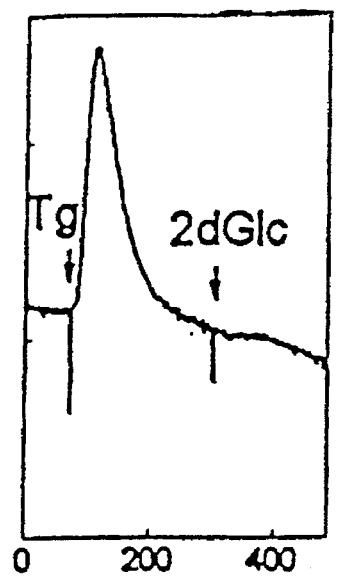
Figure 2C:
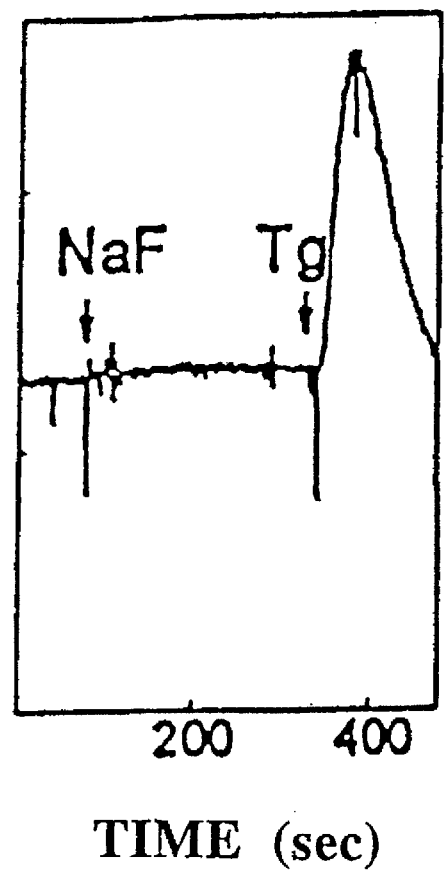

To demonstrate that 2-deoxyglucose was itself affecting cytoplasmic calcium pools, [calcium]$_i$ was monitored prior to and after the addition of 2-deoxyglucose. Addition of a 5-fold excess of 2-deoxyglucose in a buffer containing 1 mM EGTA caused a rapid release of calcium from an intracellular pool (FIG. 2A). To ascertain if this release was from endoplasmic reticulum stores, thapsigargin, which selectively inhibits the endoplasmic reticulum calcium ATPase, was added prior to 2-deoxyglucose (FIG. 2B). This addition of thapsigargin allowed detection of the rapid leakage of calcium from the endoplasmic reticulum store that is normally balanced by the calcium ATPase's activity and resulted in depletion of the 2-deoxyglucose-sensitive pool. When the drug was added after the release by 2-deoxyglucose (FIG. 2A), a diminished thapsigargin-sensitive calcium pool was detected. Although ATP concentrations were diminished by the presence of 2-deoxyglucose (Table I), other inhibitors such as NaF and 5-thioglucose showed equally profound effects on ATP levels but caused no release of calcium nor depletion of thapsigargin-sensitive stores (FIG. 2C.). Since the absence of glucose also resulted in loss of responsiveness and an increase in initial cytoplasmic calcium levels (FIG. 1C.), extracellular glucose was necessary to maintain this endoplasmic reticulum calcium pool.

TABLE I

| ATP Content of J774 Cells 4 Minutes after Addition of Nutrients/Inhibitors | |
|---|---|
| NUTRIENT/INHIBITOR | ATP CONTENT (pmol/$10^5$ cells ± s.e.m.) |
| 5 mM Glucose | 188 ± 12 |
| 5 mM Glucose + 5 mM pyruvate | 226 ± 15 |
| 5 mM Pyruvate | 180 ± 16 |
| 25 mM 2dGlc + 5 mM Glc + 5 mM pyruvate | 153 ± 12 |
| 1 mM NaF + 5 mM Glc + 5 mM pyruvate | 139 ± 12 |

Cellular ATP levels were determined using an ATP assay kit (Calbiochem) based on firefly luciferase-catalyzed oxidation of d-luciferin as described above. ATP calibrations containing the sugars and inhibitors were assessed and none interfered with the assay. Analyses were performed on 5 independent sets of cells.

The restricted metabolism of 2-deoxyglucose inside a cell limits its conversion to predominantly 2-deoxyglucose-6-phosphate. The normal metabolite, glucose-6-phosphate, has been shown in vitro to enhance up to 8-fold the ATP-dependent uptake of calcium into the endoplasmic reticulum stores of liver, kidney, and pancreatic cells by providing a negative counter-ion necessary for increased sequestration. This effect was not seen in liver microsomes exposed to 2-deoxyglucose-6-phosphate (data not shown).

EXAMPLE 7

Figures 3A, 3B:
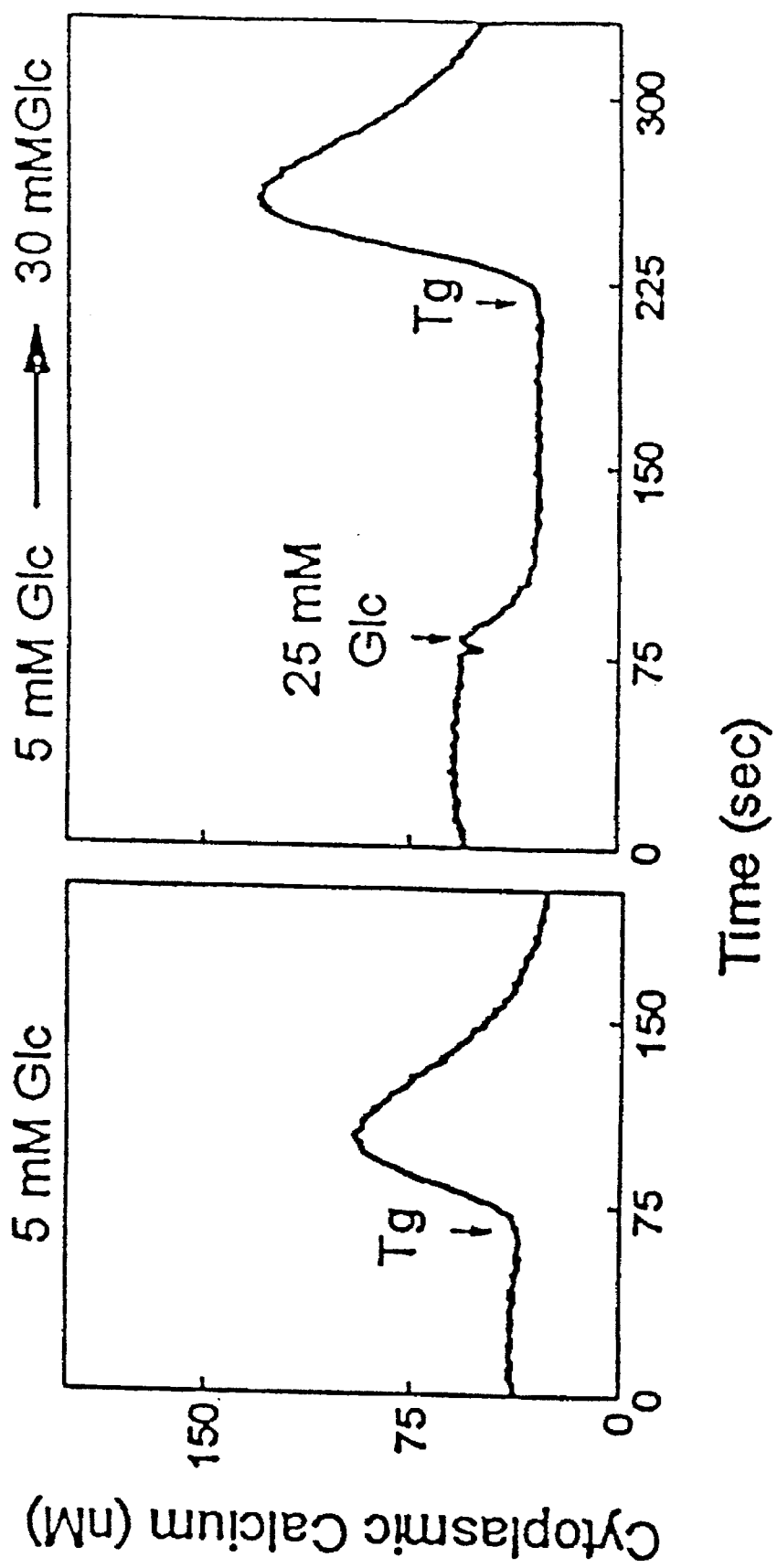
FIG. 3A shows the effects on intracellular calcium concentrations when thapsigargin (Tg) was added to deplete the intracellular stores of calcium.
FIG. 3B shows that 25 mM Glc was added prior to the addition of thapsigargin.
Figure 4:
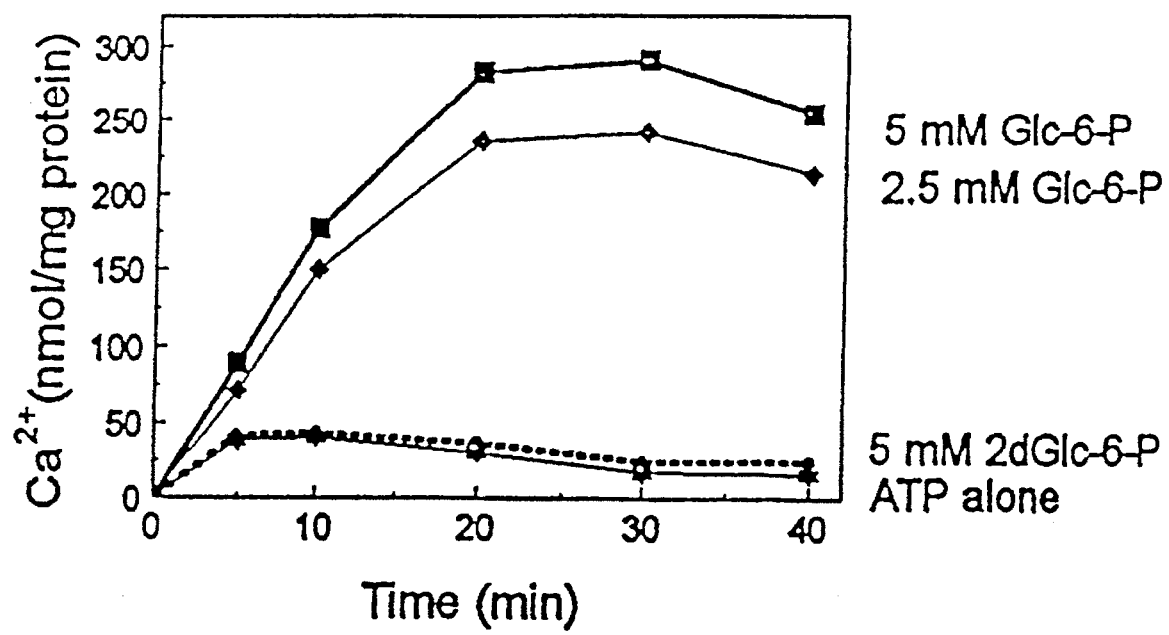
FIG. 4 shows Glc-6-P but not 2dGlc-6-P enhances $^{45}Ca^{2+}$ uptake in liver microsomes. Liver microsomes were prepared and resuspended in assay buffer containing 5 mM ATP alone or 5 mM ATP with either 5 mM Glc-6-P, 2.5 mM Glc-6-P, or 5 mM 2dGlc-6-P. Aliquots were removed at the indicated times and filtered. The amount of $^{45}Ca$ associated with the microsomes was determined by scintillation counting.

To determine if these results were due to the osmotic effects of 2dGlc addition, two experiments were carried out. In the first, the concentration of 2dGlc was decreased to 5 mM. This concentration of 2dGlc was sufficient to evoke a release of calcium from thapsigargin-sensitive stores when the ambient Glc concentration was reduced to 1 mM (data not shown). Thus, the ratio between Glc and 2dGlc concentrations is critical, as was seen for the 2dGlc-mediated inhibition of phagocytosis in both macrophages (Michl et al., 1976) and neutrophils (Boxer et al., 1976). As a second control that addresses both the osmotic effects of 2dGlc addition and the possibility of short-term ATP depletion due to sugar phosphorylation by hexokinase, 25 mM Glc was added to cells initially in 5 mM Glc (FIG. 3). In contrast to the results with 2dGlc, a decrease in cytoplasmic free calcium was observed, accompanied by a subsequent increase in the thapsigargin-releasable calcium pool. Thus, the added Glc facilitated an increased sequestration of cytoplasmic calcium into the endoplasmic reticulum. This result was most striking in cells in which the calcium pools were partially depleted but in no case was an increase in $[Ca^{2+}]_i$, such as that which accompanies 2dGlc addition, observed. The restricted metabolism of 2dGlc inside a cell limits its conversion to predominantly 2dGlc-6-P. As noted in the introduction, the analogous normal metabolite, Glc-6-P, has been shown in vitro to enhance the ATP-dependent uptake of calcium into the microsomes prepared from liver, kidney, and pancreatic cells by providing a negative counter-ion necessary for increased sequestration. Relevant to the studies in J774 cells reported above, the increase in calcium sequestration that is seen in the presence of Glc-6-P in liver microsomes was not seen when the microsomes were exposed to 2dGlc-6-P (FIG. 4).

EXAMPLE 8

Glc-6-P and $Ca^{2+}$ sequestration

Figure 5:
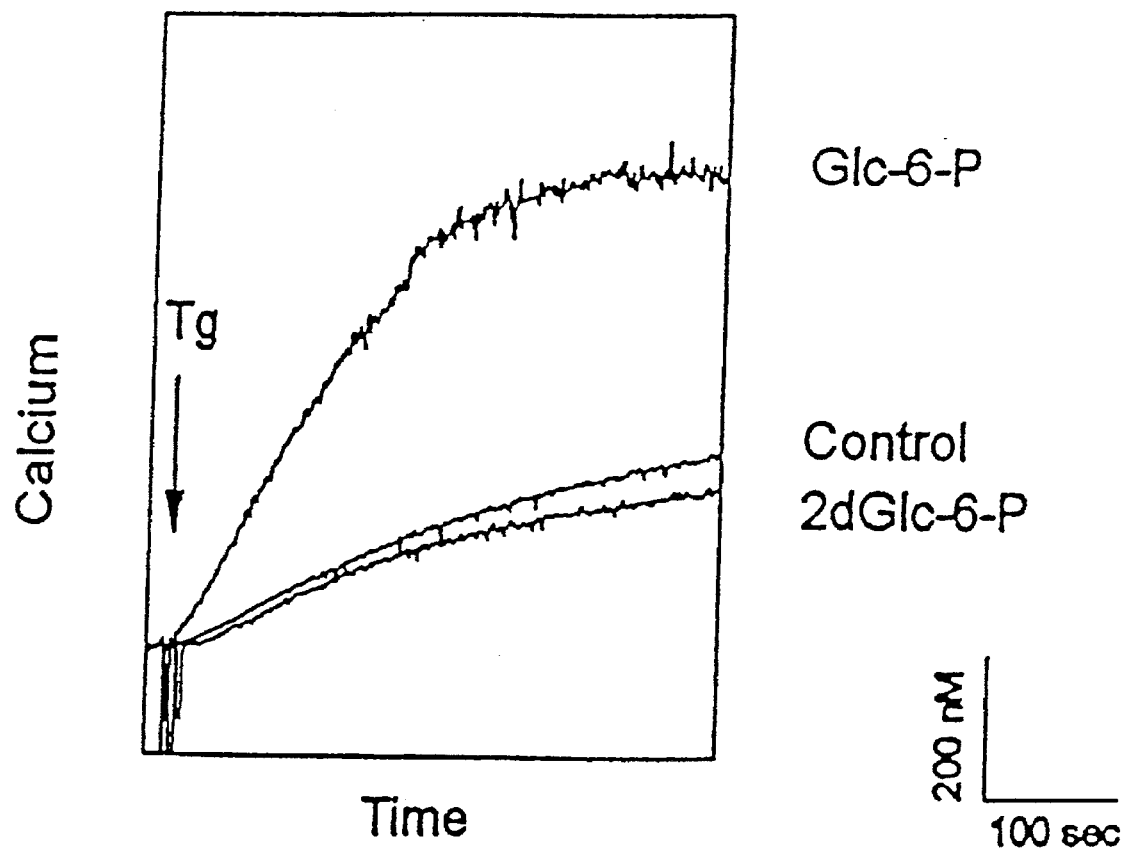
FIG. 5 shows that thapsigargin-releasable $Ca^{2+}$ is enhanced in permeabilized J774 cells in the presence of Glc-6-P but not 2dGlc-6-P. J774 cells were suspended at $10^7$ cells/ml in IB, a buffer mimicking the intracellular ionic composition. Prior to starting the experiment the calcium concentration in the buffer was lowered to 500 nM using a chelating resin, CHELEX 100. 1 mM Fura-2 pentapotassium salt, was added. The cells were permeabilized with digitonin (24 mg/ml) in the presence of ATP (2 mM) alone, ATP and Glc-6-P (5 mM), or ATP and 2dGlc-6-P (5 mM). Thapsigargin (Tg; 200 nM) was then added to assess the amount of calcium sequestered within the endoplasmic reticulum pools, as measured by the increase in calcium available for interaction with the extraorganeller Fura-2.

To demonstrate that Glc-6-P plays a role in calcium sequestration in J774 cells that is comparable to that seen in liver and to further establish that the effects reported above were not due to ATP depletion, Glc-6-P was added to permeabilized J774 cells. The cells were permeabilized with digitonin in the presence of 2 mM ATP and 2M Fura-2 in a buffer containing 500 nM calcium. Thapsigargin was then added and the resultant increase in extraorganellar $[Ca^{2+}]$ was used as an indicator of the size of the previously sequestered calcium pool. This increase was nearly three-fold larger in the presence of 5 mM Glc-6-P than in its absence or in the presence of 5 mM 2dGlc-6-P (FIG. 5). Thus, both the effects on calcium sequestration and the inhibition of phagocytosis with 2dGlc is due to a competition that results in a decrease in the import of Glc-6-P into the er and, concomitantly, an inability to maintain adequate intracellular calcium stores for signal transduction.

Figure 6A:
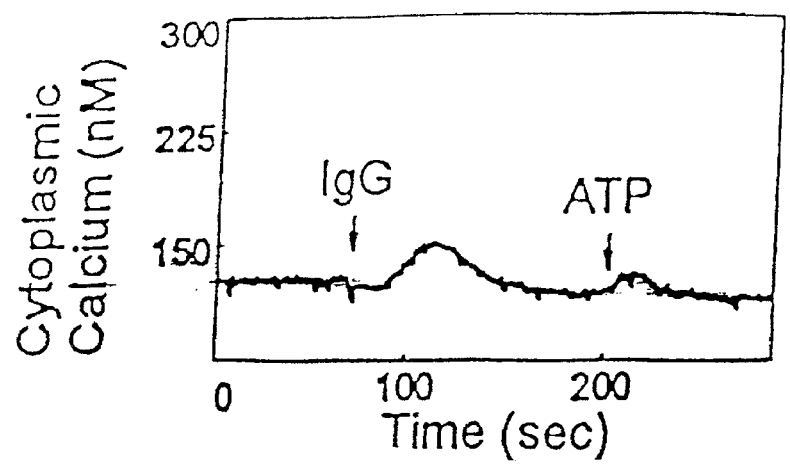
FIG. 6A shows the cells were resuspended in HBS-EGTA containing 5 mM Glc, and aggregated IgG (250 mg/ml) was added followed by 10 mM ATP. In an independent series of experiments intracellular stores were released by the addition of thapsigargin (Tg) to cells suspended in (FIG. 6b) HBS-EGTA buffer.

In non-excitable cells, the initial $IP_3$-mediated release of calcium from intracellular pools is followed by the entry of additional calcium through the plasma membrane. This influx of extracellular calcium serves to refill the intracellular stores and is referred to as capacitative $Ca^{2+}$ entry. The effect on calcium signaling when such an influx is prevented by the removal of extracellular calcium is seen in FIG. 6A. J774 cells stimulated in the absence of extracellular calcium displayed a somewhat depressed response to aggregated IgG but the subsequent calcium signal upon the addition of 10 mM ATP was markedly diminished (compare with FIG. 1A). The capacitative entry of calcium is independent of $IP_3$ generation and is apparently triggered by the depletion of endoplasmic reticulum calcium. The molecule that signals this loss of calcium from the endoplasmic reticulum and results in calcium entry through the plasma membrane has been partially characterized and termed calcium influx factor (CIF). CIF was found to be stored in the endoplasmic reticulum prior to calcium depletion, to have a mass of less than 500 daltons, to contain phosphate, and to be sensitive to periodate oxidation, as might be expected for a carbohydrate derivative. Thus, the present invention shows that Glc-6-P was critical to endoplasmic reticulum calcium stores, were consistent with the possibility that Glc-6-P might be a precursor in intra-endoplasmic reticulum CIF production and prompted an examination of the effects of 2dGlc and Glc deprivation on capacitative calcium entry in J774 cells.

Figure 6B:
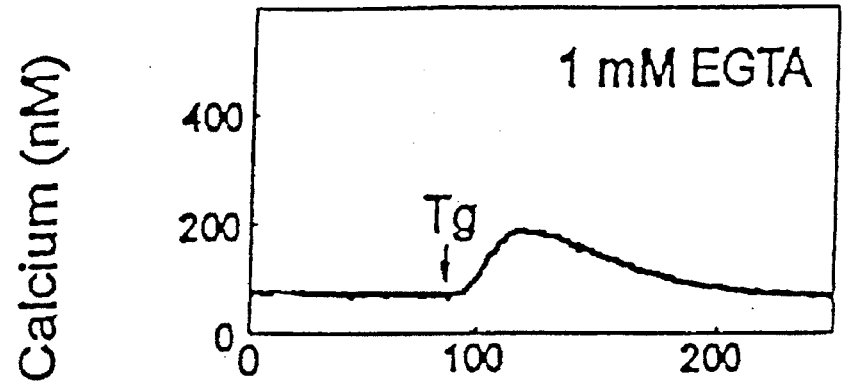
FIG. 6 shows the capacitative entry of calcium in J774 cells. The cells were loaded with Fura-2AM.
(FIG. 6c) HBS containing 2.5 mM calcium.
(FIG. 6d) HBS-EGTA buffer followed by the addition of $CaCl_2$ as indicated to produce a free calcium concentration of 2.5 mM.
Figure 6C:
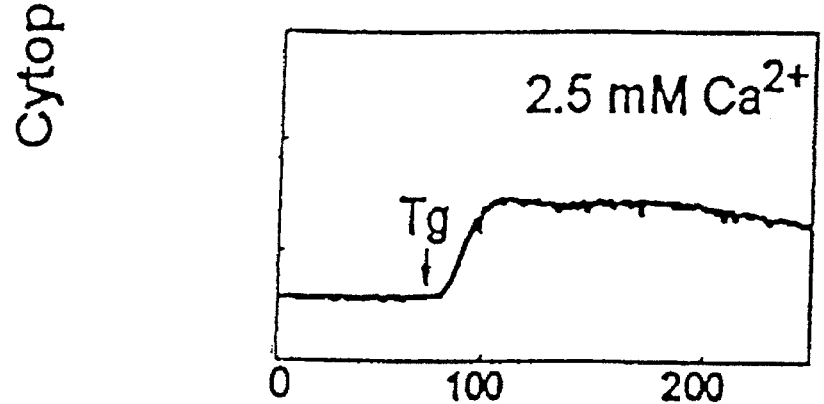
Figure 6D:
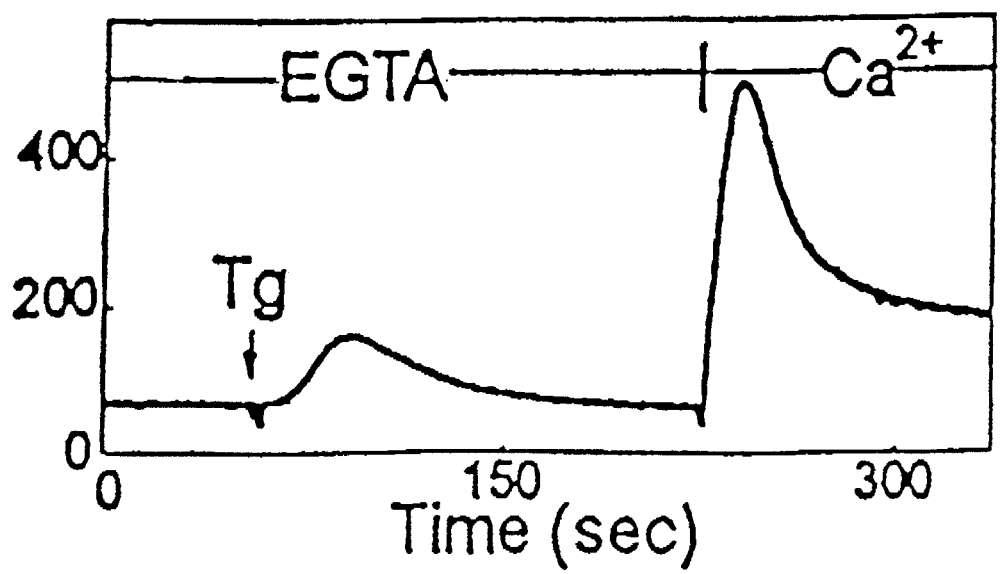

When thapsigargin, which irreversibly depletes endoplasmic reticulum stores, was added to these cells in the absence of extracellular $Ca^{2+}$ (FIG. 6b), only a transient increase in $[Ca^{2+}]_i$ was seen. However, in the presence of extracellular $Ca^{2+}$ the release of $Ca^{2+}$ from intracellular stores was augmented by a secondary sustained increase in $[Ca^{2+}]_i$ (FIG. 6c). This reflects the continuous activation of $Ca^{2+}$ influx across the plasma membrane that characterizes the capacitative entry of $Ca^{2+}$ following thapsigargin treatment. This effect could be better visualized when intracellular endoplasmic reticulum $Ca^{2+}$ pools were depleted with thapsigargin in the absence of extracellular $Ca^{2+}$, and $Ca^{2+}$ was then added to initiate the capacitative entry (FIG. 6d). A transient increase in $[Ca^{2+}]_i$ to nearly 500 nM was seen as $Ca^{2+}$ entered through the activated capacitative pathway and a steady state level was subsequently achieved, presumably when the activity of plasma membrane $Ca^{2+}$ATPases balanced the capacitative influx into the cell. The rapid increase in $[Ca^{2+}]_i$ supports the assumption that CIF was released upon the addition of thapsigargin and that the capacitative influx channels remained activated.

The depletion of intracellular $Ca^{2+}$ stores caused by 2dGlc alone did not elicit a capacitative response (data not shown). In addition, when thapsigargin treatment was followed by exposure to 2dGlc, the capacitative entry was markedly diminished (FIG. 7b). Increasing the time of exposure to 2dGlc, either before or after thapsigargin addition, resulted in a more pronounced inhibition (FIG. 7c and data not shown). This inhibition was independent of a decrease in overall ATP generation within the cell, since addition of NaF under similar conditions did not have any effect on the capacitative response (data not shown).

Figure 8A:
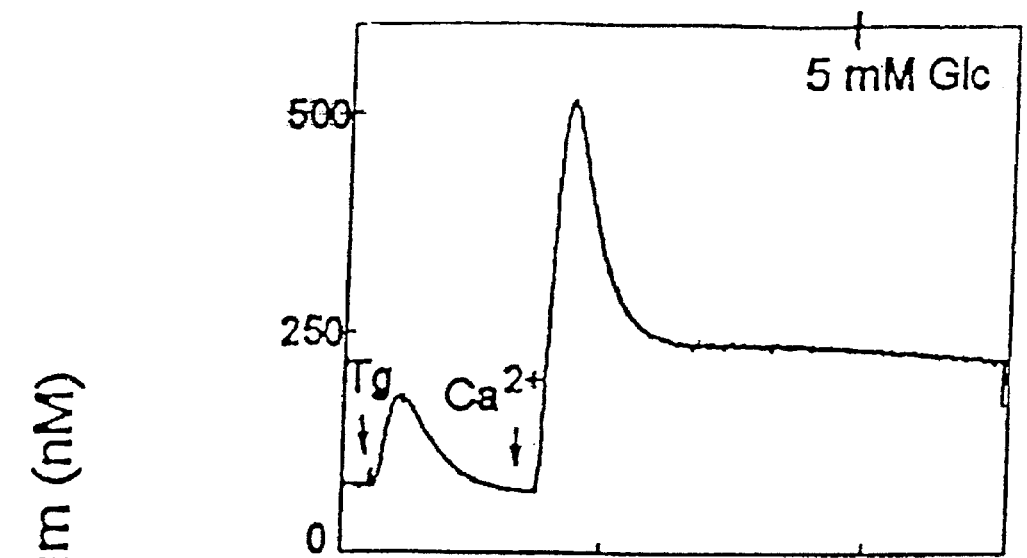
FIG. 8A shows the result when Fura-2AM loaded J774 cells were suspended in HBS-EGTA buffer containing 5 mM Glc and 5 mM pyruvate. Thapsigargin (Tg) was added, followed by calcium, while [calcium]$_i$ was monitored.
Figure 8B:
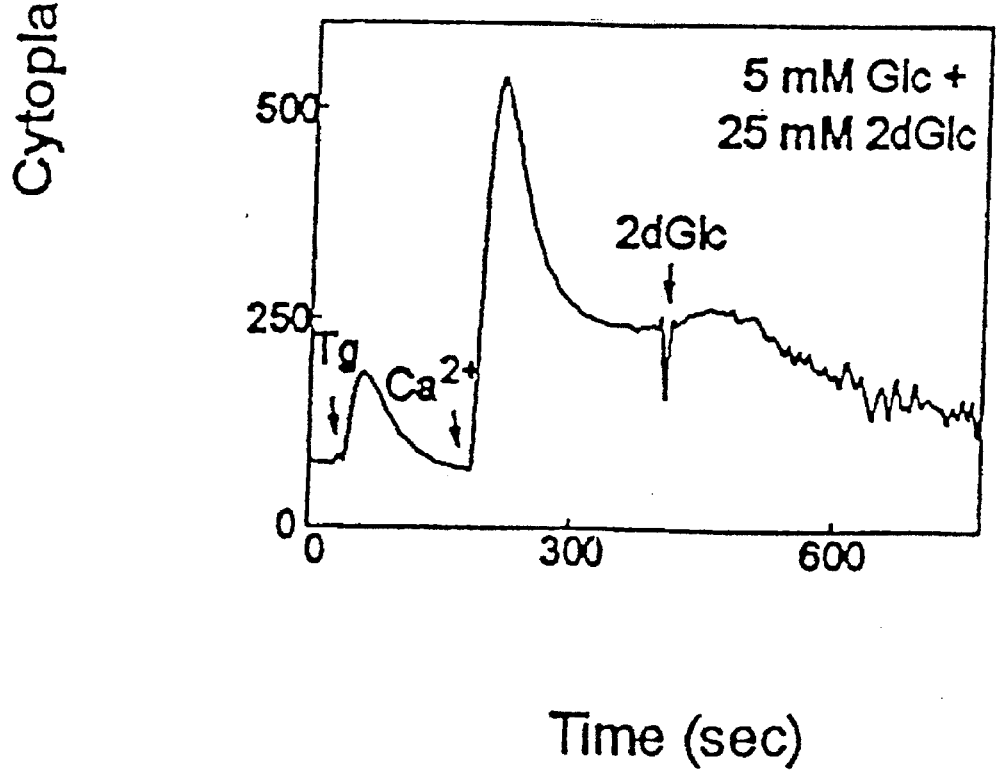
FIG. 8B shows the result when 25 mM 2dGlc was added after calcium.
Figure 8C:
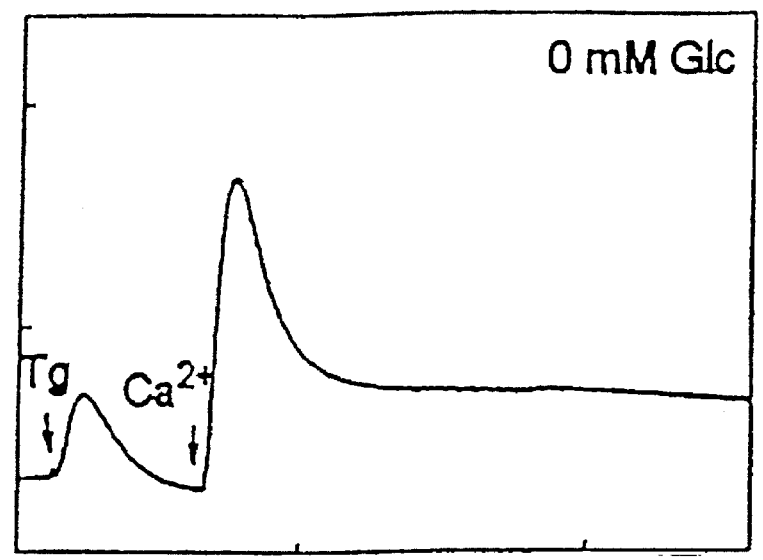
FIG. 8C shows the result when thapsigargin and calcium were added to cells suspended in HBS-EGTA containing 5 mM pyruvate but no Glc.
Figure 8D:
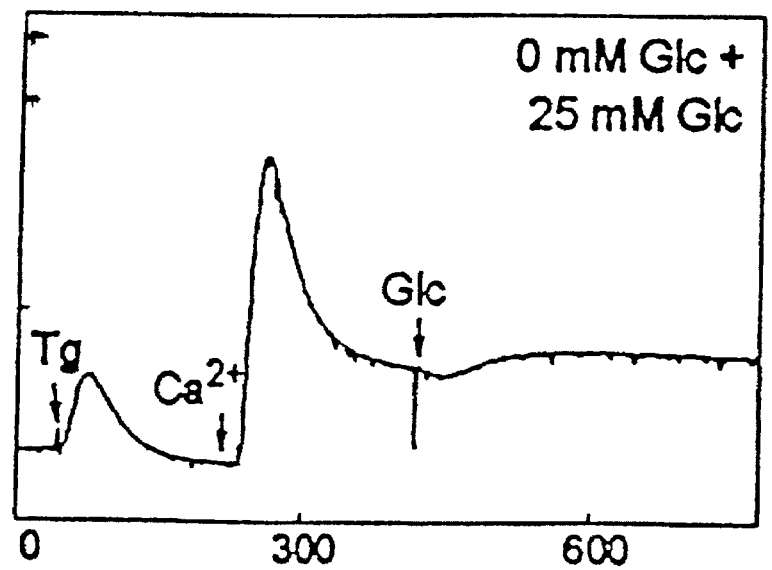
FIG. 8D shows the result when 25 mM Glc was added after the initiation of capacitative entry in the absence of Glc but in the presence of 5 mM pyruvate.

The addition of 2dGlc after the initiation of capacitative entry resulted in a rapid decrease in $[Ca^{2+}]_i$, suggesting a decrease in the rate of $Ca^{2+}$ influx (FIG. 8b). The effect of Glc deprivation on capacitative entry was also shown. The omission of Glc from the buffer resulted in an attenuation of the $Ca^{2+}$ entry (FIG. 8c relative to 8a), and a partial recovery in the steady state $Ca^{2+}$ influx was seen when Glc was added back to the cells (FIG. 8d). Thus, the presence of Glc is necessary for the optimal and on-going activation of the capacitative pathway.

EXAMPLE 9

Figure 9:
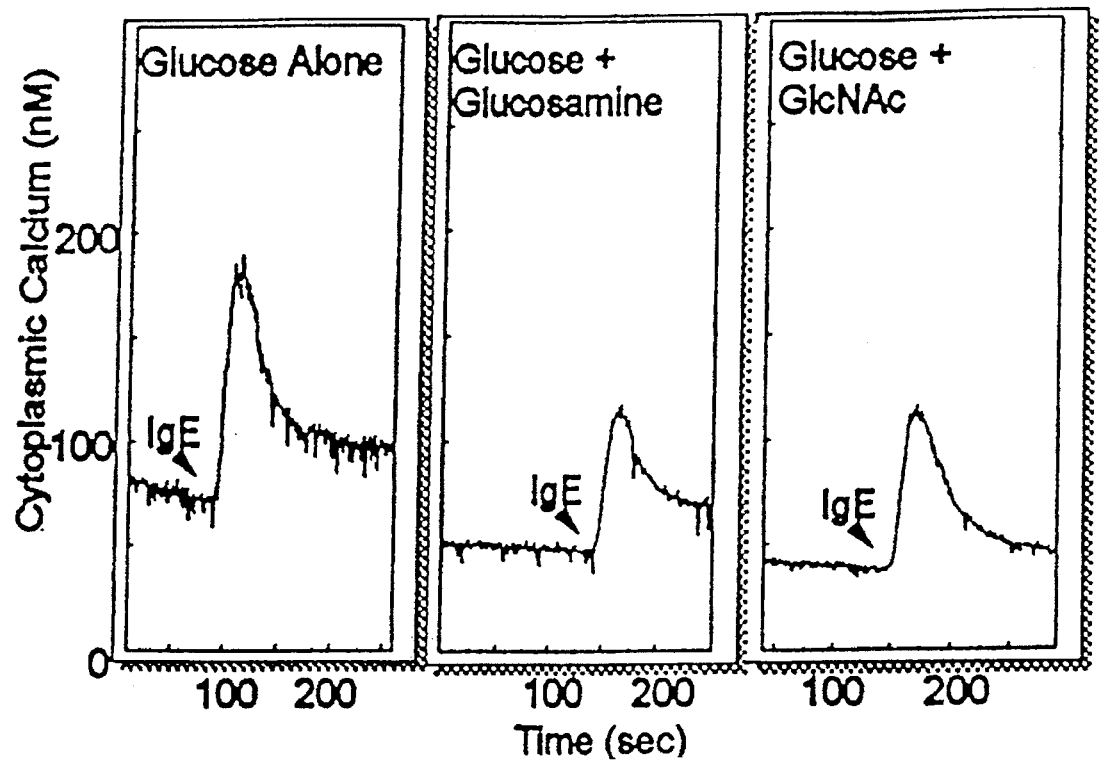
FIG. 9 shows the effect of glucose-6-phosphate inhibitors on calcium release in the RBL cell line. RBL cells were incubated in either 5 mM glucose alone or 5 mM glucose+25 mM glucosamine or n-acetylglucosamine for 15 minutes. The cells were then loaded with Fura-2AM as previously described in the presence of the same sugars. The cells were then assessed for cytoplasmic calcium in the presence of extracellular EGTA. The response in calcium concentration was significantly decreased following preincubation with either glucosamine or acetylglucosamine.

Glucose-6-phosphate Uptake inhibitors decrease $Ca^{++}$ release in RBL cell line The RBL cell line is routinely used as an in vitro model of mast cells. In the absence of extracellular calcium, IgE (the agonist which normally triggers mast cells to release histamine) produces a peak calcium release from intracellular stores of nearly 200 nM in the presence of 5 mM glucose (FIG. 9). A two minute pre-treatment with equimolar glucosamine (FIG. 9) or N-acetylglucosamine (FIG. 9) resulted in a dimimution of baseline calcium as well as a significant decrease in the peak height of the calcium response. Thus, the present invention also discloses that inhibitors of glucose-6-phosphate uptake also regulate intracellular calcium in mast cells and also decrease release of secreted markers such as histamine and $\beta$-N-acetylglucosaminidase.

EXAMPLE 10

Human alveloar macrophages are dependent on glucose for $Ca^{++}$ signalling and phagocytosis of P. aeruginosa. In J774 cells, the absence of glucose and/or the presence of glucose analogues inhibit $Ca^{++}$-mediated responses to IgG.

While macrophages are only one of the cell types that can initiate inflammatory reactions, these cells may be primarily responsible for the initial immune reaction to adenovirus. Pascual has identified the antibody isotype most induced (up to 90% of the titer) as being $IgG_2b$. Since distinct routes of signal transduction within the immune system result in different complements of antibody isotypes being produced, the presence of such a high titer of $IgG_2b$ suggests strong involvement of a lower respiratory, macrophage-mediated pathway in this inflammatory process.

To show that glucose and/or glucose analogues are effective immunomodulators in the CF lung, human alveolar macrophages are assessed for their glucose dependence in assays monitoring $Ca^{2+}$ signaling and phagocytosis in P. aeruginosa. Human alveolar macrophages are collected by lung lavage from patients undergoing clinically indicated bronchoscopies. While these patients have various pulmonary difficulties, their macrophages have proven relatively normal and useful for a variety of related studies. The human macrophages are used directly or cultured for 24 hours in a glucose-containing medium.

Cytoplasmic $Ca^{2+}$ Responses to Agonists and Thapsigargin

Alveolar macrophages are loaded with Fura-2AM in a procedure that has been shown to be effective with human monocyte-derived macrophages and similar to that used with J774 cells. Cytoplasmic $Ca^{2+}$ are monitored in response to aggregated IgG in the presence of 0–5 mM glucose and various concentrations of 2dglucose, glucosamine, and glucoseNAc. Preincubations in glucose and/or the analogues range from 0 to 24 hour. In addition to IgG, other agonists that have been linked to $Ca^{2+}$-dependent activation of macrophages including platelet-activating factor, histamine, and lipopolysaccharide are examined. Lastly, the effects of the analogues on thapsigargin-releasable $Ca^{2+}$ are determined. ATP measurements are carried out as described previously to determine the effects of the analgoues on overall ATP metabolism.

Glucose and glucose analogues and the phagocytosis of P. aeruginosa

P. aeruginosa are grown overnight from frozen stocks in tryptone and yeast extract (Difco) at 37° C., harvested at mid-log phase, and concentrated by centrifugation to a density of $10^9$ colony forming units/ml in physiological saline. Immediately before the assays, the bacteria's pellicle are disrupted by gentle vortexing. In some experiments, the bacteria are opsonized by tumbling the bacteria in heat-inactivated, commercially available polyclonal anti-P. aeruginosa rabbit serum. Phagocytosis assays are carried out on coverslips with bound but ingested bacteria being lysed at the end of 60 minute incubations using ice-cold lysozyme. Cells are stained with toluidine-blue and the number of phagocytosed bacteria quantitated by bright-field microscopy. Assays are carried out in various combinations of glucose and glucose analogues, utilizing pre-incubations ranging from 0 to 24 hours.

The dependency on glucose seen during the phagocytosis of non-opsonized P. aeruginosa appears to be due to interruption of a $Ca^{2+}$-mediated signaling cascade initiated by activation of the purported P. aeruginosa receptor. The binding of P. aeruginosa initiates an increase in cytoplasmic $Ca^{2+}$ using Fura-2AM-loaded macrophages. The P. aeruginosa is bound to the cell surface at 4° C. utilizing co-centrifugation to bring macrophages and bacteria into contact. The pellet is gently disrupted, added to the spectrofluorometer cuvette in a small volume at 4° C. and then diluted with 2 ml of pre-warmed media just prior to the initiation of $Ca^{2+}$ monitoring and is performed in the presence and absence of glucose and its analogues.

EXAMPLE 11

Inflammation is a major hurdle to virally based gene therapy strategies, with immune-mediated destruction of virus-infected cells leading to lung injury and premature clearance of the very cells that are expressing CFTR along with viral antigens. A CD-1 mouse model is used to show that treatment with glucose analogues modified at the 2-carbon ameliorates the inflammatory response that precedes lung injury following application of adenovirus.

Adenovirus-sensitive, pathogen-free CD-1 mice serves as the host strain, with a minimum of six animals being used in each treatment group. The animals are maintained in isolators and tested regularly for the presence of pathogens including mouse adenovirus, mouse hepatitis virus, pneumonia virus of mice, and Sendai virus. Replication-deficient variants of Ade5 containing the -galactosidase gene (Ade-LacZ) are administered intra-tracheally (i.t.) to these animals. The adenovirus constructs are provided by Dr. Jeong Hong of UAB's CF Center. The mice receive two 50 μl doses of $10^9$ virus particles/dose at day 0 and day 14. Glucose analogues are administered twice a week, which was shown to be effective in treatment of osteoarthritis, via the same i.t. route in 50 μl doses of 50 mg/kg body weight. Administration of the glucose analogues are initiated one week prior to adenovirus challenge and continues through day 21.

Effects on Antibody-Producing Cells

Mice are untreated or treated with either glucosamine, N-acetylglucosamine or 2dglucose prior to infection with Ade-LacZ using the regimen described above. One week following the final dose of Ade-LacZ, the animals are bled and serum IgG antibody concentration to Ade5 determined by ELISA. In this assay, 96-well plates are coated with Ade5 vital particles and incubated with selected dilutions of serum samples. IgG concentrations is determined by incubation with horseradish peroxidase-conjugated anti-IgG and a soluble colorimetric substrate 3-amino-9-ethyl-carbazole.

After sufficient blood samples have been taken, the animals are sacrificed and the lungs, lower respiratory lymph nodes (LRLN), and spleens removed. The lungs are perfused with sterile physiological saline, minced into 1 cm² pieces, and digested with collagenase (300 U/ml) and DNAse (50 U/ml). Single cells are collected by filtration through a mesh. Mononuclear cells are isolated from this suspension by Ficoll-hypaque density gradient centrifugation. The mononuclear cells isolated from the lungs are adjusted to a uniform lymphocyte concentration as determined by differential analyses of cell smears stained with eosin, thiazine, and Wright-Giemsa-like stain (HemaColor, EM Diagnostic Systems). Single cell suspensions are prepared from the LRLN and spleen and further fractionated by Ficoll-hypaque density gradient centrifugation. The number of antibody-producing cells of different subtypes to Ade5 are determined by ELISPOT assays. These measurements should provide information as to the effects of glucose analogues on the magnitude of both systemic and local immune responses to Ade5 and identify the immune pathways involved.

Assessment of Lung Damage

In addition to characterizing the antibodies expressed as a result of Ade-LacZ instillation, the inflammatory state of lungs in animals treated as described above are assayed using two histochemical approaches and one biochemical assay. The first histochemical approach is a conventional histological examination of the lung. Lungs are perfused with Tissue-Tek$^R$-O.C.T. compound and frozen immediately at −20° C. 4 μm cryosections are prepared. Some of these sections are fixed with methanol, stained with hematoxylin and eosin, and examined at the light level. Random fields are selected, and the number of infiltrating monoclear cells determined by counting using a reticule. Other sections are examined using epifluorescence microscopy after being stained with an antibody to nitro-tyrosine. Lung injury and damage observed following exposure to Ade-LacZ is primarily a consequence of increased peroxynitrite formation. Although peroxynitrite is unstable, one byproduct of its reaction with proteins is the addition of a nitro group ($NO_2$) to tyrosine residues to form 3-nitro-tyrosine. The examination of lung cryosections with anti-nitro-tyrosine provides a qualitative assessment of the extent of lung damage. The biochemical approach determines byproducts of nitric oxide generation, nitrite and nitrate, using a colorimetric assay. After the infection period, the lungs are perfused with sterile buffered saline and the lungs and trachea removed en bloc. Ten ml of buffered saline are infused in the trachea and withdrawn. Cells are removed from this lavage by centrifugation, and nitrate and nitrite determined by incubating the cell-free sample with Greiss reagent (0.1% N-1-naphythlethylenediamine, 1% sulfanilamide, 5% phosphoric acid) for 10 minutes. Absorbance at 550 nm is assessed. Nitrate is reduced to nitrite using $E.\ coli$ nitrate reductase and measured in an identical manner.

Persistence of LacZ Expression

In addition to inflammation, glucose analogues also have an effect on the persistence of cells expressing foreign proteins. Adenovirus-mediated LacZ expression persists longer in nude mice than controls, and immunosuppression would be expected to have comparable effects. In order to show that glucose analogues are effective toward this end, replication-deficient Ade-LacZ is instilled in CD-1 mice in the presence or absence of varying concentrations of glucose analogues. Following 7, 14, and 21 day exposure to Ade-LacZ, the lungs is perfused with Tissue-Tek$^R$-O.C.T. compound, frozen immediately at −20° C., and 4 gm cryosections prepared. Cryosections are stained with a -galactosidase staining solution (5 mM $K_4Fe(CN)_6$, 5 mM $K_3Fe(CN)_6$, 2 mM $MgCl_2$ in phosphate buffered saline in the presence of 1 mg/ml X-gal) for 3 hours at 37° C. The expression of -galactosidase is determined qualitatively by examining these sections under low-level light microscopy. X-gal staining of control lungs occasionally results in non-specific staining. Staining of matched controls is compared to staining of experimental lungs to provide the most accurate picture of the expression of -galactosidase.

EXAMPLE 12

The present invention also provides a novel strategy for the screening of second-generation immunosuppressive therapeutics. These screenings allow one with ordinary skill in this art to assess the potency of drugs in inhibiting the uptake of Glc-6-P by the endoplasmic reticulum through either competitive inhibition of this uptake by advanced Glc analogues or through drugs that, via other mechanisms, inhibit the action of the responsible anion transporter.

Use of the subcellular microsomal fraction to Screen Glc-6-P analogues and other drugs for their effects on Glc-6-P and $Ca^{2+}$ sequestration Microsomes prepared from cells of interest, for instance mast cells or their cultured equivalents, are assessed for Glc-6-P sequestration and Glc-6-P mediated augmentation of $Ca^{2+}$ sequestration. The Glc-6-P sequestration assays involve determination of imported Glc-6-P levels as assessed either by radioisotope accumulation assays or utilizing enzyme-linked chemical assays. The sequestration of $Ca^{2+}$ utilize either radioisotope accumulation or Fura-2 or other similar $Ca^{2+}$ sensitive dyes. To get the control levels of import, the amount of Glc-6-P that is sequestered by microsomes as a function of time is determined. Concomitantly, the effects of Glc-6-P on the rate of $Ca^{2+}$ sequestration is documented. Therapeutics are screened for their ability to interfere with Glc-6-P accumulation and for their ability to interfere with the Glc-6-P augmentation of $Ca^{2+}$ sequestration relative to that seen in controls. Drugs screened utilizing these protocols include phosphorylated analogues of glucose, such as N-acetylglucosamine-6-P, 2dGlc-6-P and Glc-6-P, as well as other analogues of Glc. In addition, compounds that may be active because of their effects on anion transporters are also screened for their capacity to inhibit both Glc-6-P sequestration and Glc-6-P augmented $Ca^{2+}$ sequestration.

Secondly, novel drugs are screened utilizing intact cells and monitoring their capacity to respond to appropriate stimuli, such as aggregated IgG or IgE, through the monitoring of cytoplasmic $Ca^{2+}$ levels using a cytoplasmic $Ca^{2+}$ indicator such as Fura-2 AM. Compounds include analogues of Glc that are imported via the glucose transporter and phosphorylated by hexokinase to produce the corresponding sugar-6-phosphates, e.g. 2dGlc, glucosamine and N-acetylglucosamine. Other analogues are also developed. In addition to analogues of Glc, potential inhibitors of anion transporters are monitored. This approach is novel since it utilizes putative inhibitors of anion transporters in order to determine if $Ca^{2+}$, a cation, is being sequestered properly. These two approaches provide an efficient screening of multiple new potential drug candidates.

Glucose-6-phosphatase has been used as an intralumenal marker for the endoplasmic reticulum in many cell types, although its activity is much higher in certain tissues (such as liver) than in others. In liver, glucose-6-phosphate is imported into the er as part of the glycogen degradation pathway. After cleavage, glucose is exported to the cytoplasm and from there is transported through the plasma membrane to the bloodstream. Glucose-6-phosphatase levels are significantly lower in most tissues than in liver. Thus, for at least one reason, a broad involvement of glucose-6-phosphate in calcium regulation has never been suggested prior to the present invention. The present invention shows that the critical step in providing a counter-ion is the import of glucose-6-phosphate rather than its cleavage to $P_i$. In brain microsomes, the imported glucose-6-phosphate responsible for additional sequestered calcium remains uncleaved.

In view of the present invention, it appears that the involvement of glucose-6-phosphate in maintaining appropriate er calcium stores, as demonstrated here, provides a rationale for the complications associated with certain genetic diseases in which import of glucose-6-phosphate into the er is defective. These data also show that import rather than cleavage of glucose-6-phosphate is critical.

The enhancement of calcium sequestration seen with glucose-6-phosphate in permeabilized cells requires millimolar levels of glucose-6-phosphate. A pertinent challenge to the relevance of these data to responses in intact cells centers on whether these concentrations of glucose-6-phosphate are reached within the cytoplasm. While estimates of overall glucose-6-phosphate concentrations range from 0.1 to 1 mM, local concentrations and the phenomenon of substrate channeling may also be relevant. There is now substantial evidence that metabolic channeling characterizes both the glycolytic and citric acid pathways, in which substrates are efficiently delivered from enzyme to enzyme without equilibration with other pools of the same substrates. In effect, this creates local pools of metabolites at high concentrations relative to those found in other areas of the cell. Glucose-6-phosphate is formed primarily by two reactions in most cells. One involves the phosphorylation of glucose by hexokinase. A significant portion of hexokinase has been established as being membrane associated, attributable in part to binding to mitochondria and in part to the endoplasmic reticulum. Interestingly, hexokinase has been shown to move in response to activating stimuli from a relatively uniform distribution within the cytoplasm of macrophages to actin-rich areas near the cell periphery. A similar movement of calcium sequestering organelles detected with an antibody specific for the endoplasmic reticulum calcium ATPase was recently reported for macrophages during antibody-mediated phagocytosis, consistent with the possibility of co-localization and glucose-6-phosphate channeling.

Glycogen and the enzymes responsible for its conversion to glucose-6-phosphate also appear to be associated with the endoplasmic reticulum. In liver, large glycogen stores are regulated by cAMP-dependent enzymes, and during hypoglycemic conditions significant levels of glucose are returned to the blood supply via the pathway discussed above. However, in other tissues such as leukocytes, smooth muscle, or brain glycogen stores have shorter half-lives and degradation is initiated in response to stimuli such as phagocytosis that lead to increases in cytoplasmic calcium. The prevailing thought has been that this degradation, even in the presence of adequate exogenous glucose, was necessary because of increases in energy required, for instance, for contraction or phagocytosis. However, glycogen may provide a means of creating high levels of glucose-6-phosphate necessary for the re-sequestration of calcium following the respective stimuli.

The role of glucose-6-phosphate as a modulator of cytoplasmic calcium is supported by the finding that phosphoglucomutase is a cytoplasmic glycoprotein which, in excitable cells, becomes fully glycosylated when cytoplasmic calcium levels increase. In addition, increases in cytoplasmic calcium led to an increase in phosphoglucomutase's membrane association, especially with the endoplasmic reticulum or, in skeletal muscles, with the sarcoplasmic reticulum. Phosphoglucomutase participates in the conversion of glucose-1-phosphate to glucose-6-phosphate and the channeling of this glucose-6-phosphate into microsomes. In addition to phosphoglucomutase, other enzymes important to glycogen degradation including glycogen phosphorylase have also been found selectively bound to the surface of the sarcoplasmic reticulum in skeletal muscle. The mechanism for association for phosphatase-1, the phosphatase responsible for activating glycogen phosphorylase, is dependent upon a targeting subunit that selectively binds both the phosphatase and glycogen to the surface of the sarcoplasmic reticulum.

The present invention demonstrates that adding an excess of 2-deoxyglucose or depleting glucose resulted in an inhibition of capacitative calcium entry. Negatively charged anions like glucose-6-phosphate or its possible metabolite (CIF) are necessary to balance calcium's charge within the endoplasmic reticulum. If these anions are released along with calcium because of this charge pairing, as is the case with phosphate and succinate, then one of the unknown facets of CIF physiology would be elucidated. CIF may accompany calcium into the cytoplasm because of charge pairing.

The relationship established between glucose metabolism and calcium sequestration by the endoplasmic reticulum may also have relevance to the induction of the subset of heat-shock or stress proteins referred to as the glucose-regulated proteins (GRPs). Two of these proteins, GRP78 and GRP94, were originally characterized because of their increased synthesis following glucose deprivation. It now appears that stimuli that lead to the accumulation of malfolded or abnormal proteins, such as inhibitors of glycosylation, amino acid analogues, or 2-mercaptoethanol, induce the synthesis of the GRP's. In addition, these proteins are also induced by agents that deplete the endoplasmic reticulum of calcium, such as EGTA, thapsigargin, and the calcium ionophores A23187 and ionomycin. Endoplasmic reticulum calcium depletion leads to activation of the GRP's through the same well-conserved promoter region as the other stresses, and may serve as is an inducer because the absence of calcium leads to malfolded proteins that do not leave the endoplasmic reticulum. GRP94 has been characterized as a low-affinity, high-capacity calcium binding protein, while GRP78 was initially identified as the immunoglobulin heavy chain binding protein (BiP). Both of these proteins have been implicated in protein folding processes within the endoplasmic reticulum, as has a third member of the 6RP family, 6RP170. The up-regulation of these proteins has been proposed to result in an accomodation that allows for continued proteins synthesis and folding in the absence of intra-endoplasmic reticulum calcium.

In addition to glucose deprivation, the presence of the glucose analogues 2-deoxyglucose and glucosamine also lead to induction of the GRP's. All three of these stimuli have been assumed to be inducers because of their inhibition of protein glycosylation. However, Morin et al. determined that in L1210 cells 3 mM glucosamine was sufficient to induce synthesis of GRP78 without resulting in a decrease of [$^3$H]Man incorporation or lectin agglutination. In addition, Lin et al., demonstrated that the form of GRP170 produced in response to glucose deprivation, glucosamine, A23187, and, to a variable extent, 2-deoxyglucose, is characterized by the presence of high mannose-type chains, in contrast to the 150 kDa form seen following tunicamycin treatment. These data suggest that with these treatments a response other than inhibition of core N-linked glycosylation results in GRP induction. The present invention demonstrates that calcium depletion from the endoplasmic reticulum due to the absence of glucose or the presence of its analogues is the responsible stimulus. If this is true, the large range of cells that respond to glucose deprivation by inducing GRP synthesis would support an equally broad role for glucose-6-phosphate as a critical anion in endoplasmic reticulum calcium sequestration. The effects of glucosamine on the balance of calcium between the endoplasmic reticulum and cytoplasm may also contribute to the toxicity of glucosamine that was initially ascribed to depletion of adenine or uridine nucleotides. However, the finding that the endoplasmic reticulum in treated cells becomes fragmented led to the suggestion that cellular membranes may be the primary target. A similar fragmentation of the endoplasmic reticulum is seen in some cells following treatment with calcium ionophore.

The present invention illustrates an intriguing interplay between calcium regulation and glucose metabolism. In J774 cells, glucose-6-phosphate is critical for adequate calcium sequestration within the endoplasmic reticulum, and, more speculatively, for providing a precursor necessary for CIF synthesis. A variety of other phenomena as diverse as sperm capacitation, neural activity in hippocampus and retina, and T cell-mediated cytolysis have also been shown to be dependent on glucose in a manner independent of total cellular ATP. The data may also have implications to pathological phenomena brought about by either abnormally high or low levels of the sugar, contributing, for instance, to the altered regulation of calcium that characterizes various cells from diabetics including the phagocytic capabilities of neutrophils.

Any patents or publications mentioned in this specification are indicative of the levels of those skilled in the art to which the invention pertains. These patents and publications are herein incorporated by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. The present examples along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. A method of inhibiting the import of glucose-6-phosphate into the endoplasmic reticulum of a cell, comprising the step of adminstering a pharmacologically effective dose of a glucose analogue to said cell, said analogue being phosphorylated at its 6-carbon after uptake by said cell, wherein Said inhibitor is given by is given by a route of administration selected from the group consisting of oral administration, nasal administration and inhalation administration.

2. The method of claim 1, wherein said analogue is modified at the number 2 carbon.

3. The method of claim 1, wherein said analogue is a competitive inhibitor of glucose-6-phosphate uptake.

4. The method of claim 3, wherein said inhibitor is selected from the group consisting of 2-deoxyglucose, glucosamine, and N-acetylglucosame.

5. The method of claim 4, wherein said inhibitor is administered to said at a concentration of from about 0.1 mM to about 20 mM.

6. The method of claim 1, wherein said calcium-sequestering organelle is the endoplasmic reticulum.

7. The method of claim 1, wherein said analogue is a non-competitive inhibitor of glucose-6-phosphate uptake.

* * * * *